United States Patent
Malet

(10) Patent No.: US 10,105,310 B2
(45) Date of Patent: Oct. 23, 2018

(54) COSMETIC COMPOSITION COMPRISING PEBA

(75) Inventor: Frédéric Malet, Rouen (FR)

(73) Assignee: ARKEMA FRANCE, Colombes (FR)

( * ) Notice: Subject to any disclaimer, the term of this patent is extended or adjusted under 35 U.S.C. 154(b) by 883 days.

(21) Appl. No.: 13/807,783

(22) PCT Filed: Jun. 29, 2011

(86) PCT No.: PCT/FR2011/051509
§ 371 (c)(1),
(2), (4) Date: Feb. 20, 2013

(87) PCT Pub. No.: WO2012/001298
PCT Pub. Date: Jan. 5, 2012

(65) Prior Publication Data
US 2013/0156833 A1   Jun. 20, 2013

(30) Foreign Application Priority Data
Jul. 1, 2010   (FR) ...................... 10 55288

(51) Int. Cl.
| | | |
|---|---|---|
| *A61K 47/10* | (2017.01) | |
| *A61Q 19/00* | (2006.01) | |
| *A61K 8/90* | (2006.01) | |
| *A61K 47/34* | (2017.01) | |
| *A61Q 1/10* | (2006.01) | |
| *A61Q 1/14* | (2006.01) | |
| *A61Q 15/00* | (2006.01) | |

(52) U.S. Cl.
CPC ................ *A61K 8/90* (2013.01); *A61K 47/34* (2013.01); *A61Q 1/10* (2013.01); *A61Q 1/14* (2013.01); *A61Q 19/00* (2013.01); *A61K 2800/10* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 6,010,715 A | 1/2000 | Wick et al. | |
| 6,455,059 B1 | 9/2002 | Albers et al. | |
| 6,629,961 B1 | 10/2003 | Israelsson et al. | |
| 6,638,259 B1 | 10/2003 | Palasis et al. | |
| 8,039,525 B2 | 10/2011 | Loyen et al. | |
| 2003/0153685 A1 | 8/2003 | Corley | |
| 2004/0186263 A1* | 9/2004 | Pavlin | 528/232 |
| 2010/0234499 A1 | 9/2010 | Sugihara et al. | |
| 2010/0305232 A1 | 12/2010 | Loyen et al. | |

FOREIGN PATENT DOCUMENTS

| | | |
|---|---|---|
| EP | 1686142 A1 | 8/2006 |
| EP | 2053093 A1 | 4/2009 |

OTHER PUBLICATIONS

Lange et al. ("Lange", 1965, J. Soc. Cosmetic Chemist, 16, 563-570).*
International Search Report for PCT/FR2011/051509 (dated Sep. 21, 2011).
International Preliminary Report on Patentability for PCT/FR2011/051509 (dated Jan. 8, 2013).
"Clariant Extends Masterbatch Range for Medical Applications", Additives for Polymers, Elsevier Advanced Technology, vol. 2008, No. 3 (Feb. 27, 2008) XP022501275 pp. 3-4.

\* cited by examiner

*Primary Examiner* — Misook Yu
*Assistant Examiner* — Kauser M Akhoon
(74) *Attorney, Agent, or Firm* — Millen, White, Zelano and Branigan, P.C.

(57) ABSTRACT

The present invention relates to a composition comprising from 0.1 to 30% by weight of copolymer comprising polyether blocks and polyamide blocks (PEBA), and from 70 to 99.9% by weight of a medium which is acceptable in the cosmetics industry, in the perfumery industry and/or in the pharmaceutical industry. The present invention also relates in particular to a process for incorporating a copolymer comprising polyether blocks and polyamide blocks into a cosmetic, perfumery and/or pharmaceutical medium. The subject matter of the present invention is also the use of a copolymer comprising polyether blocks and polyamide blocks (PEBA) for producing a cosmetic, pharmaceutical or perfumery product, said PEBA being incorporated in the form of a composition in accordance with the invention.

12 Claims, No Drawings

COSMETIC COMPOSITION COMPRISING PEBA

FIELD OF THE INVENTION

The present invention relates to a cosmetic composition comprising an elastomeric thermoplastic polymer, in particular a copolymer with polyether blocks and polyamide blocks (PEBA hereinafter).

The present invention relates in particular to the use of these PEBAs in cosmetic, pharmaceutical or perfumery products, and to cosmetic, pharmaceutical, or perfumery compositions comprising at least one PEBA.

PRIOR ART

Thermoplastic polymers intended for cosmetic or medical use are generally in the form of powder. Consequently, formulation with these powders generally requires intermediate steps of grinding, or sieving, in the form of fine powder with D50 generally below 10 or 20 μm, and preliminary dispersion of this powder in a liquid so that the texture of the final product incorporating the powder is perfectly homogeneous and has a uniform appearance. Moreover, the great volatility of fine powders means that their use in formulation requires many precautions. It is notably difficult for formulators to quantify exactly and reproducibly the powder content of the formulas.

Among the elastomeric thermoplastic polymers, copolymers with polyether blocks and polyamide blocks (polyether block amide copolymers, PEBA) are known for their great flexibility (very wide range), their elasticity, chemical resistance and thermal stability, their dynamic properties, their stable properties at temperatures from −40° C. at 80° C., their waterproof-breathable properties, their resistance to UV, etc.

These properties are already exploited in applications as varied as sports equipment, glasses, textiles, automobiles, and coating of materials with fine powders of PEBA. However, these properties of PEBAs have never been exploited in the area of cosmetics, where the challenges facing formulators in terms of textures and feel are more and more demanding and varied.

The aim of the present invention is therefore to supply compositions comprising PEBA, ready for use, which make PEBA easier to use by formulators, in that they are usable directly (by simple incorporation) in cosmetic formulations, for example for endowing them with a particular texture. Thus, the formulator no longer needs to undertake preliminary adaptation of the form of the PEBAs sold commercially in the form of powder or granules. Moreover, the PEBA contents in the formulations are easily quantifiable and reproducible.

The present invention notably aims to provide a simple method (comprising the fewest possible steps) for manufacturing said PEBA compositions that are ready to use.

Surprisingly, the applicant has also shown that the use of copolymers with polyether blocks and polyamide blocks makes it possible to manufacture said cosmetic compositions with innovative textures and properties.

DETAILED DESCRIPTION OF THE INVENTION

The present invention therefore relates to a composition comprising:

from 0.1 to 30 wt % of polyether-block-amide copolymer (PEBA), and
from 70 to 99.9 wt % of a medium that is acceptable in cosmetics, in perfumery and/or in pharmacy.

PEBA:

The "copolymers with polyether blocks and polyamide blocks" abbreviated to "PEBA" result from the polycondensation of polyamide blocks with reactive ends with polyether blocks with reactive ends, such as, among others:

1) polyamide blocks with diamine chain ends with polyoxyalkylene blocks with dicarboxylic chain ends,
2) polyamide blocks with dicarboxylic chain ends with polyoxyalkylene blocks with diamine chain ends, obtained by cyanoethylation and hydrogenation of aliphatic dihydroxylated alpha-omega polyoxyalkylene blocks called polyether diols,
3) polyamide blocks with dicarboxylic chain ends with polyether diols, the products obtained being, in this particular case, polyetherester amides.

The polyamide blocks with dicarboxylic chain ends are obtained, for example, by condensation of polyamide precursors in the presence of a chain-limiting dicarboxylic acid. The polyamide blocks with diamine chain ends are obtained for example by condensation of polyamide precursors in the presence of a chain-limiting diamine.

The number-average molecular weight Mn of the polyamide blocks is between 400 and 20 000 g/mol and preferably between 500 and 10 000 g/mol.

The polymers with polyamide blocks and polyether blocks can also comprise units distributed randomly.

Three types of polyamide blocks can be used advantageously.

According to a first type, the polyamide blocks are obtained by condensation of a dicarboxylic acid, in particular those having from 4 to 20 carbon atoms, preferably those having from 6 to 18 carbon atoms, and an aliphatic or aromatic diamine, in particular those having from 2 to 20 carbon atoms, preferably those having from 6 to 14 carbon atoms.

As examples of dicarboxylic acids, we may mention 1,4-cyclohexyldicarboxylic acid, butanedioic, adipic, azelaic, suberic, sebacic, dodecanedicarboxylic, octadecanedicarboxylic acids and terephthalic and isophthalic acids, as well as dimerized fatty acids.

As examples of diamines, we may mention tetramethylenediamine, hexamethylenediamine, 1,10-decamethylenediamine, dodecamethylenediamine, trimethylhexamethylenediamine, isomers of bis(4-aminocyclohexyl)methane (BACM), bis(3-methyl-4-aminocyclohexyl)methane (BMACM), and 2-2-bis(3-methyl-4-aminocyclohexyl)propane (BMACP), and para-amino-dicyclohexyl-methane (PACM), and isophoronediamine (IPDA), 2,6-bis(aminomethyl)norbornane (BAMN) and piperazine (Pip).

Advantageously, the blocks are PA4.12, PA4.14, PA4.18, PA6.10, PA6.12, PA6.14, PA6.18, PA9.12, PA10.10, PA10.12, PA10.14 and PA10.18.

According to a second type, the polyamide blocks result from the condensation of one or more alpha-omega aminocarboxylic acids and/or one or more lactams having from 6 to 12 carbon atoms in the presence of a dicarboxylic acid having from 4 to 12 carbon atoms or of a diamine. As examples of lactams, we may mention caprolactam, enantholactam and lauryllactam. As examples of alpha-omega aminocarboxylic acid, we may mention the aminocaproic, amino-7-heptanoic, amino-11-undecanoic and amino-12-dodecanoic acids.

Advantageously the polyamide blocks of the second type are of polyamide 11, of polyamide 12 or of polyamide 6.

According to a third type, the polyamide blocks result from the condensation of at least one alpha-omega aminocarboxylic acid (or a lactam), at least one diamine and at least one dicarboxylic acid.

In this case, the polyamide PA blocks are prepared by polycondensation:

of aromatic or linear aliphatic diamine or diamines having X carbon atoms;

of dicarboxylic acid or acids having Y carbon atoms; and of comonomer or comonomers {Z}, selected from lactams and alpha-omega aminocarboxylic acids having Z carbon atoms and equimolar mixtures of at least one diamine having X1 carbon atoms and at least one dicarboxylic acid having Y1 carbon atoms, (X1, Y1) being different from (X, Y), said comonomer or comonomers {Z} being introduced in a proportion by weight of up to 50%, preferably up to 20%, even more advantageously up to 10% relative to all the polyamide precursor monomers;

in the presence of a chain limiter selected from the dicarboxylic acids.

Advantageously, the chain limiter used is dicarboxylic acid having Y carbon atoms, which is introduced in excess relative to the stoichiometry of the diamine or diamines.

According to a variant of this third type, the polyamide blocks result from the condensation of at least two alpha-omega aminocarboxylic acids or of at least two lactams having from 6 to 12 carbon atoms or of a lactam and an aminocarboxylic acid not having the same number of carbon atoms optionally in the presence of a chain limiter. As examples of aliphatic alpha-omega aminocarboxylic acid, we may mention aminocaproic, amino-7-heptanoic, amino-11-undecanoic and amino-12-dodecanoic acids. As examples of lactam, we may mention caprolactam, enantholactam and lauryllactam. As examples of aliphatic diamines, we may mention hexamethylenediamine, dodecamethylenediamine and trimethylhexamethylenediamine. As an example of cycloaliphatic diacids, we may mention 1,4-cyclohexyldicarboxylic acid. As examples of aliphatic diacids, we may mention the butanedioic, adipic, azelaic, suberic, sebacic, dodecanedicarboxylic acids, the dimerized fatty acids (these dimerized fatty acids preferably have a content of dimer of at least 98%; preferably they are hydrogenated; they are marketed under the brand name "PRIPOL" by the company "UNICHEMA", or under the brand name EMPOL by the company HENKEL) and the polyoxyalkylenes—α,ω diacids. As examples of aromatic diacids, we may mention terephthalic acid (T) and isophthalic acid (I). As examples of cycloaliphatic diamines, we may mention the isomers of bis(4-aminocyclohexyl)methane (BACM), bis(3-methyl-4-aminocyclohexyl)methane (BMACM), and 2-2-bis(3-methyl-4-aminocyclohexyl)propane (BMACP), and para-amino-dicyclohexyl-methane (PACM). The other diamines commonly used can be isophoronediamine (IPDA), 2,6-bis(aminomethyl)norbornane (BAMN) and piperazine.

As examples of polyamide blocks of the third type, we may mention the following:

6.6/6 in which 6.6 denotes hexamethylenediamine units condensed with adipic acid. 6 denotes units resulting from condensation of caprolactam.

6.6/6.10/11/12 in which 6.6 denotes hexamethylenediamine condensed with adipic acid. 6.10 denotes hexamethylenediamine condensed with sebacic acid. 11 denotes units resulting from condensation of aminoundecanoic acid. 12 denotes units resulting from condensation of lauryllactam.

The polyether blocks can represent 5 to 85 wt % of the polyether-amide-block copolymer. The molecular weight Mn of the polyether blocks is between 100 and 6000 g/mol and preferably between 200 and 3000 g/mol.

The polyether blocks consist of alkylene oxide units. These units can be for example ethylene oxide units, propylene oxide units or tetrahydrofuran (which leads to polytetramethylene glycol chains). Thus, the following are used: PEG (polyethylene glycol) blocks, i.e. those consisting of ethylene oxide units, PPG (propylene glycol) blocks, i.e. those consisting of propylene oxide units, PO3G (polytrimethylene glycol) blocks, i.e. those consisting of polytrimethylene glycol ether units (these copolymers with polytrimethylene ether blocks are described in document U.S. Pat. No. 6,590,065), and PTMG blocks, i.e. those consisting of tetramethylene glycol units, also called polytetrahydrofuran. The PEBA copolymers can comprise several types of polyethers in their chain, and the copolyethers can be of block or random type.

It is also possible to use blocks obtained by ethoxylation of bisphenols, such as bisphenol A for example. These last-mentioned products are described in patent EP613919.

The polyether blocks can also consist of ethoxylated primary amines. As examples of ethoxylated primary amines we may mention the products of formula:

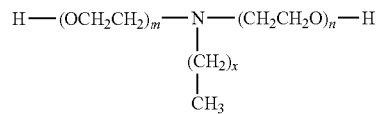

in which m and n are between 1 and 20 and x is between 8 and 18. These products are commercially available under the brand name NORAMOX® from the company CECA and under the brand name GENAMIN® from the company CLARIANT.

The flexible polyether blocks can comprise polyoxyalkylene blocks with $NH_2$ chain ends, and said blocks can be obtained by cyanoacetylation of aliphatic dihydroxylated alpha-omega polyoxyalkylene blocks called polyether diols. More particularly, Jeffamines can be used (for example Jeffamine® D400, D2000, ED 2003, XTJ 542, commercial products from the company Huntsman, also described in patent documents JP2004346274, JP2004352794 and EP1482011).

The polyether diol blocks are either used as such and copolycondensed with polyamide blocks with carboxylic ends, or they are aminated to be transformed into polyether diamines and condensed with polyamide blocks with carboxylic ends. The general method of two-step preparation of PEBA copolymers having ester bonds between the PA blocks and the PE blocks is known and is described, for example, in French patent FR2846332. The general method of preparation of the PEBA copolymers of the invention having amide bonds between the PA blocks and the PE blocks is known and described, for example in European patent EP1482011. The polyether blocks can also be mixed with polyamide precursors and a diacid chain limiter to make polymers with polyamide blocks and polyether blocks having units distributed randomly (one-step method).

Of course, the designation PEBA in the present description of the invention also relates to the PEBAX® marketed by Arkema, to the Vestamid® marketed by Evonik®, to the Grilamid® marketed by EMS, and to the Kellaflex® marketed by DSM or to any other PEBA from other suppliers.

Advantageously, the PEBA copolymers have PA blocks of PA 6, PA 11, PA 12, PA 6.12, PA 6.6/6, PA 10.10 and/or PA 6.14, preferably PA 11 and/or PA 12 blocks; and PE blocks of PTMG, of PPG and/or of PO3G. The PEBAs based on PE blocks consisting predominantly of PEG are to be classed among the hydrophilic PEBAs. The PEBAs based on PE blocks consisting predominantly of PTMG are to be classed among the hydrophobic PEBAs.

Advantageously, said PEBA used in the composition according to the invention is obtained at least partially from bio-sourced raw materials.

"Renewable raw materials" or "bio-sourced raw materials" means materials that comprise bio-sourced carbon or renewable carbon. In fact, in contrast to materials derived from fossil materials, the materials composed of renewable raw materials contain $^{14}C$. The "renewable carbon content" or "bio-sourced carbon content" is determined by applying standards ASTM D 6866 (ASTM D 6866-06) and ASTM D 7026 (ASTM D 7026-04). As an example, the PEBAs based on polyamide 11 are derived at least partly from bio-sourced raw materials and have a bio-sourced carbon content of at least 1%, which corresponds to a $^{12}C/^{14}C$ isotope ratio of at least $1.2 \times 10^{-14}$. Preferably, the PEBAs according to the invention comprise at least 50 wt % of bio-sourced carbon based on the total weight of carbon, which corresponds to a $^{12}C/^{14}C$ isotope ratio of at least $0.6 \times 10^{-12}$. This content is advantageously higher, notably up to 100%, which corresponds to a $^{12}C/^{14}C$ isotope ratio of $1.2 \times 10^{-12}$, in the case of PEBAs with PA 11 blocks and PE blocks comprising PO3G, PTMG and/or PPG derived from renewable raw materials.

"Medium acceptable in cosmetics, perfumery or pharmacy" means in the sense of the invention any product that does not cause irritation or reaction on the skin, keratin fibers (eyelashes, hair) or the nails.

Advantageously, said medium comprises at least one component selected from water, alcohols, alcoholic solutions, lipid compounds, carbohydrate compounds, hydrocarbons, synthetic polymers, natural polymers, and/or plant extracts.

Advantageously, the composition according to the invention has at least one of the following forms: dispersion, solution, emulsion, microemulsion, nanoemulsion, dry emulsion, suspension, aerosol, gel, compact gel, gum, plastic gum, paste, mousse, cream, powder, loose powder, compact powder, expanded powder, butter, film, elastic film, and mixtures thereof.

Advantageously, said medium comprises an aqueous phase comprising at least 50% water. The water can be softened water, demineralized water and/or sterilized water, depending on its degree of purification, thermal water, etc.

The aqueous phase can further comprise alcohols with the number of carbons in the carbon chain not exceeding 6, which are water-soluble, such as ethanol, isopropanol. Alcoholic solutions obtained by simple mixing of these alcohols with water are also usable in the aqueous phase; as well as glycols, such as ethylene glycol, propylene glycol; polyols, such as glycerol or glycerin, sorbitol, sorbitol syrup.

Polyoxyethylene glycols (PEG) can also be used as solvents in said aqueous phase. The carboxyvinyl polymers (carbomers or Carbopol), cyanoacrylic polymers; carbohydrate compounds, such as polysaccharides or polysaccharides extracted from algae (alginates, carrageenans), wood (cellulose and derivatives thereof), sap from trees (gum arabic, tragacanth gum), seeds or pips (pectin, guar gum, carob gum, starch), leaves (aloe gel); glycoproteins or proteoglycans; carbohydrate esters and ethers can also be included in the composition of the aqueous phase, notably as thickening or gelling agents of the aqueous phase.

Preservatives, hydrophilic emulsifiers, colorants, humectants, gelling agents, hydrophilic active ingredients and any other hydrophilic cosmetic agent can be included in the composition of said aqueous or hydrophilic phase.

Advantageously, said medium comprises an oily phase comprising at least 50% of organic solvent selected from fatty esters, fatty alcohols, fatty acids, and mixtures thereof.

The fatty alcohols in the sense of the invention are alcohols whose carbon chain comprises at least 7 carbons, preferably from 7 to 10 carbons, so that they are liquid at room temperature. They are water-insoluble but the presence of hydroxyl endows them with a slight affinity for water. We may notably mention benzyl alcohol, which performs the role of solvent and preservative.

The fatty acids in the sense of the invention are organic acids that are present in lipids. Their carbon chain is of variable length (from C4 to C30) and they can be saturated or unsaturated. The saturated fatty acids are solid at room temperature (25° C.), except the C4 and C6 acids. The unsaturated fatty acids are liquid. As examples, we may mention lauric acid, stearic acid, oleic acid.

The fatty esters result either from the combination of a fatty acid with a short-chain alcohol (for example isopropyl palmitate or myristate which form liquid fatty esters), or from the combination of a fatty acid with a fatty alcohol (for example isostearyl isostearate), or from the combination of a short-chain acid with a fatty alcohol with variable chain length (for example benzoic acid with a C13-C15 fatty alcohol forming benzoates of fatty alcohols).

Other lipid compounds may be present in said oily phase, such as vegetable oils such as jojoba oil, castor oil, peanut oil, sunflower oil, borage oil, coconut oil; animal oils; these oils may or may not be modified chemically; synthetic oils such as synthetic mono-, di- and triglycerides, for example caprylic capric triglycerides; unsaponifiables, notably avocado oil, soybean oil, corn oil, karite oil; butters, notably karite butter, copra butter, cocoa butter; waxes with melting point above 50° C. of vegetable origin (carnauba wax, candelilla wax) or animal origin (beeswax, propolis wax); phospholipids, notably soybean lecithin.

Said oily phase can also include mineral hydrocarbons: mineral oils, petroleum jellies, paraffins, isoparaffins; silicones such as silicone oils such as dimethicone, phenylmethicone, volatile silicones such as cyclomethicone or emulsifying silicones.

The oily phase can also contain silicas, silicates, notably aluminum silicate and/or magnesium silicate, clay, kaolin, montmorillonite, bentone, bentonite, hectorite, which thicken the oily phase.

Antioxidants, pigments, fillers such as talc, nylon, silica, lipophilic active ingredients and any other lipophilic cosmetic agent can also be included in the composition of said oily phase.

Advantageously, said medium further comprises from 0.1 to 30 wt % of surfactant based on the total weight of PEBA.

Surfactant, in the sense of the invention, means:
surfactants of synthetic origin which are themselves divided into two groups, ionic surfactants (anionic such as sodium lauryl sulfate or salts of fatty acid, cationic such as ammonium stearyl chloride, or amphoteric such as betaine derivatives) and nonionic surfactants with HLB in the range from 0 to 20, for example sorbitan esters (Span, Tween) and polyethoxylated fatty alcohols; and surfactants of natural origin, such as cholesterol, lecithin, saponin, and proteins such as casein.

Preferably, the surfactant according to the invention is selected from the anionic surfactants and the nonionic surfactants. The surfactant is advantageously selected from the salts of alkyl ether sulfate and of polyoxyalkylene, the salts of dialkylsulfosuccinate, the salts of fatty acid and the ethylene oxide/propylene oxide copolymers, and mixtures thereof.

Preferably, the composition according to the invention comprises:
from 0.1 to 30% of PEBA,
from 40 to 99.9% of oily phase and/or of aqueous phase,
from 0 to 30% of surfactant, preferably from 0.1 to 20% of surfactant, based on the total weight of the composition.

Advantageously, the composition according to the invention further comprises a lipophilic or hydrophilic thickening or gelling agent such as those described above.

Further addition of acid or of base optionally makes it possible to adjust the pH of the composition of the invention, and/or can modify the solubility of the PEBA notably in aqueous dispersions of PEBA. In particular, inorganic salts (such as NaCl, KCl or others) can affect the interactions between the chains of the PEBA and the solvent.

According to a preferred embodiment of the invention, the composition forms a dispersion of PEBA dissolved in an oily phase dispersed in an aqueous phase in the presence of a surfactant.

According to another advantageous embodiment of the invention, the composition forms a dispersion of PEBA dissolved in an aqueous phase dispersed in an oily phase in the presence of a surfactant.

The present invention also relates to a method of incorporating a polyether-block-amide copolymer in a cosmetic, perfumery and/or pharmaceutical medium, said method comprising at least one step selected from: mixing, dispersing, homogenizing, high-pressure homogenizing, forming a solution, diluting, dissolving, gelling, thickening, emulsifying, refining, making into a paste, treating thermally, drying, lyophilizing, baking, extruding, grinding, granulating, spraying, filtering, and successive or simultaneous mixtures of several of these steps.

Advantageously, said method comprises the steps of:
adding directly or gradually, preferably with stirring in the range from 100 to 20 000 rev/min, polyether-block-amide copolymer (PEBA) to a medium acceptable in cosmetics, in perfumery, and/or in pharmacy, the PEBA/medium weight ratio being in the range from 40/60 to 1/99, inclusive; and
heating said mixture at a temperature in the range from 40 to 190° C., preferably in the range from 60 to 180° C., preferably from 70 to 130° C., preferably at a pressure in the range 1 to 100 bar, for a time in the range from 5 to 120 minutes, preferably from 5 to 60 minutes, preferably from 10 to 30 minutes;
the steps of addition and of heating being either simultaneous, or successive, applied in this order or in the reverse order.

Preferably, the method according to the invention comprises addition of 0.1 to 30% of polyether-block-amide copolymer (PEBA) in 70 to 99.9% of a medium acceptable in cosmetics and/or in perfumery, the mixture obtained representing 100%.

Preferably, the PEBA used in the method of the invention is in the form of powder with D50 in the range from 1 to 150 µm, preferably in the range from 1 to 100 µm, preferably from 1 to 50 µm, preferably from 1 to 30 µm.

In the sense of the invention, D50 corresponds to the average size by volume, i.e. the value of the particle size that divides the population of particles examined exactly in two. D50 is measured according to standard ISO 9276—parts 1 to 6: "Representation of data obtained by granulometric analysis".

Advantageously, in the method of the invention, the medium that is acceptable in cosmetics, in perfumery and/or in pharmacy comprises an aqueous phase (or a polar solvent, preferably protic) comprising at least 50% water based on the weight of aqueous phase and/or an oily phase comprising at least 50% of organic solvent based on the weight of oily phase, said organic solvent being selected from fatty esters, fatty alcohols, fatty acids and mixtures thereof.

Preferably, the method of the invention comprises the following steps:
dissolving the PEBA in the oily phase;
emulsifying the solution of PEBA obtained in the aqueous phase containing at least one surfactant, preferably selected from anionic surfactants and nonionic surfactants.

Advantageously, the method of the invention comprises a step consisting of emulsifying the PEBA with melting point Tm in the aqueous phase containing at least one surfactant selected from anionic surfactants and nonionic surfactants, at a temperature above Tm, and with stirring at a sufficient shear rate so that D50 of the emulsified PEBA droplets is in the range from 0.1 to 50 µm, preferably in the range from 0.1 to 20 µm, in the range from 0.1 to 10 µm, preferably with stirring at more than 1000 rev/min, preferably at more than 10 000 rev/min.

The present invention further relates to the use of a polyether-block-amide copolymer (PEBA) for making a cosmetic, pharmaceutical or perfumery product, said PEBA being incorporated in the form of a composition according to the invention.

The present invention notably relates to a composition according to the invention as defined above, said composition being a colored, non-colored and/or transparent product selected from the following products:
makeup products for the face and the human body, such as foundation, tinted cream, loose or compact powder, eye shadow, mascara, eye liner, lipstick, nail varnish;
care products for the face and the human body, such as cream, milk, lotion, mask, peeling product, cleansing and/or makeup removal products, deodorants, antiperspirants, shaving products, epilatories;
hair products, such as shampoos, products for shaping the hair, styling products, anti-dandruff products, products against hair loss, products against dryness of the hair, hair dyes, bleaching products;
perfumery products, such as perfume, milk, cream, perfumed loose or pressed powder.

EXAMPLES

The following examples illustrate the present invention without limiting its scope. Unless stated otherwise, all percentages are by weight.

Example 1

PEBA 1 used: copolymer with PA12 blocks and PTMG blocks with respective molecular weights in g/mol (850-2000). Media used, acceptable in cosmetics and/or perfumery: several solvents are tested, respectively: ethanol, diethyl phthalate, dipropylene glycol, then phenoxyethanol.

Procedure:

In order to compare the solubility of PEBA 1 in these various solvents, a solvent/PEBA 1 mixture is prepared (20 and 30 wt % of PEBA 1 based on the total weight of the mixture) in 15-ml glass tubes, which are then stoppered. The tubes, placed in a boat, are then immersed in an oil bath, the temperature of which is increased gradually (in successive stages). The tubes are agitated manually at each temperature stage.

Table 1 below records the temperature of the oil and the time in minutes at this temperature. The tubes contain clear solutions of low viscosity starting from different temperatures. The term solution indicates a medium that is properly clear. The term "solution limit" indicates a medium that is rather opaque.

TABLE 1

| Tests of example 1 | Medium | PEBA (%) | 71° C. 30 min | 87° C. 1 h | 102° C. 90 min | 131° C. 75 min |
|---|---|---|---|---|---|---|
| Test 1 | Ethanol | 30 | solution | solution | — | — |
| Test 2 | Ethanol | 20 | solution | solution | — | — |
| Test 3 | Diethyl phthalate | 30 | block | block | block | solution |
| Test 4 | Diethyl phthalate | 20 | solution limit | solution | solution | — |
| Test 5 | Dipropylene glycol | 30 | block | block | solution | — |
| Test 6 | Dipropylene glycol | 20 | block | solution | solution | — |
| Test 7 | Phenoxy-ethanol | 30 | block | solution | solution | — |
| Test 8 | Phenoxy-ethanol | 20 | solution limit | solution | solution | — |

Example 2

Disperse, with stirring (12 000 rev/min, using a mixer of the Ultra-turrax type), 40 wt % of each solution of PEBA obtained in example 1 added gradually to 60 wt % of an aqueous phase consisting of water containing 5 wt % of a surfactant based on the total weight of the mixture. The surfactant used is sodium polyoxyalkylene lauryl ether sulfate. The emulsion obtained is stirred for 5 minutes after the end of addition. The temperature during addition and stirring is maintained in the range from 70 to 90° C., then the aqueous dispersion of PEBA obtained is cooled in the ambient air.

D50 of the particles (droplets) of PEBA in the dispersions from example 2 is in the range from 0.5 to 5 µm.

The aqueous dispersions from example 2 are stable at 50° C. for several months.

The solutions (example 1) or dispersions (example 2) obtained according to the invention can advantageously be incorporated in a cosmetic formulation as in the following examples:

Example 3

Formulation of Cream:

| | Cream | % |
|---|---|---|
| phase A (oily) | stearic acid | 12.5 |
| | cetyl alcohol | 0.5 |

-continued

| | Cream | % |
|---|---|---|
| phase B (aqueous) | triethylamine | 2 |
| | glycerin | 10 |
| | Test 2 of Example 1 | 7 |
| | water | q.s. 100 |
| | preservative (Germall plus) | 0.1 |

Procedure:

Heat A and B separately to a temperature of about 90° C.;

Pour B into A, with stirring (in a deflocculator, of the Silverson® homogenizer type) for at least 5 minutes and until a homogeneous emulsion is obtained;

Continue stirring slowly, gradually lowering the temperature to 30° C., and add the preservative.

A white protective cream is obtained, of "smooth" appearance on setting and during application.

Example 4

Formulation of Milk for Makeup Removal:

| | Milk for makeup removal | % |
|---|---|---|
| phase A (oily) | stearic acid | 3.5 |
| | paraffin oil | 9 |
| | cetyl alcohol | 0.9 |
| | PEG monostearate (Tefose 1500) | 0.9 |
| phase B (aqueous) | triethylamine | 1.8 |
| | water | q.s. 100 |
| | Composition of test 6 | 5 |
| | water | q.s. 100 |
| | preservative (Phenonip) | 0.2 |

Procedure:

Heat A and B separately to 80° C.

Slowly pour B into A, with stirring (in a deflocculator) for at least 5 minutes and until a homogeneous emulsion is obtained;

Continue stirring slowly, gradually lowering the temperature to 30° C., and add the preservative.

A fluid milk for makeup removal is obtained, which when applied on the skin, effectively absorbs the impurities (makeup, excess sebum) from the skin.

Example 5

Mascara Formulation, O/W:

| | Mascara O/W | % |
|---|---|---|
| phase A (oily) | beeswax | 5 |
| | ozokerite | 7 |
| | carnauba wax | 3 |
| | stearic acid | 5 |
| | glyceryl stearic | 5 |
| | Sepicid | 0.5 |
| phase B (aqueous) | water | q.s. 100 |
| | triethylamine | 1.5 |
| | propylene glycol | 5 |
| | black iron | 10 |

|  | Mascara O/W | % |
|---|---|---|
|  | oxide | |
|  | Composition of test 6 in the form of aqueous dispersion according to example 2 | 7.5 |
| active ingredient | water | 1 |
|  | D-panthenol | 0.5 |

Procedure:

Heat the oily phase to 90° C.;

Disperse the pigment (black iron oxide) cold in the Ultraturax in water with propylene glycol and triethylamine;

Heat the aqueous phase thus obtained to 90° C. and add the composition of test 6 in the form of aqueous dispersion according to example 2;

Pour the aqueous phase B into the oily phase A with rapid stirring (200 rev/min) in a deflocculator for 5 minutes;

Cool the emulsion obtained with moderate stirring to a temperature of 25-30° C., then add the active ingredient.

A mascara is obtained for "flexible" curving of the eyelashes. The composition according to the invention gives a film-forming effect, coating and curving the eyelashes, which remain flexible.

The invention claimed is:

1. A composition comprising:
   from 0.1 to 30 wt % of polyether-block-amide copolymer (PEBA) and
   from 70 to 99.9 wt % of a medium that is acceptable in cosmetics, in perfumery and/or in pharmacy, comprising an aqueous phase comprising at least 50% water,
   said composition having at least one of the following forms: dispersion, solution, emulsion, microemulsion, nanoemulsion, dry emulsion, suspension, aerosol, gel, compact gel, gum, plastic gum, paste, mousse, cream, powder, loose powder, compact powder, expanded powder, butter, film, elastic film, or a mixture thereof.

2. The composition as claimed in claim 1, in which said medium comprises at least one component that is alcohols, alcoholic solutions, lipid compounds, carbohydrate compounds, hydrocarbons, synthetic polymers, natural polymers, and/or plant extracts.

3. The composition as claimed in claim 1, in which said medium further comprises an oily phase comprising at least 50% of organic solvent selected from fatty esters, fatty alcohols, fatty acids and mixtures thereof.

4. The composition as claimed in claim 1 in which said medium comprises from 0.1 to 30 wt % of surfactant based on the total weight of PEBA.

5. The composition as claimed in claim 4 in which the surfactant is an anionic surfactant or nonionic surfactant.

6. The composition as claimed in claim 4 in which the surfactant is a salt of alkyl ether sulfate and of polyoxyalkylene, a salt of dialkylsulfosuccinate, a salt of fatty acid and ethylene oxide/propylene oxide copolymers, or a mixture thereof.

7. The composition as claimed in claim 1, characterized in that it comprises:
   from 0.1 to 30% of PEBA,
   from 40 to 99.9% of oily phase and/or of aqueous phase,
   from 0 to 30% of surfactant,
   based on the total weight of the composition.

8. The composition as claimed in claim 1, further comprising a thickener.

9. The composition as claimed in claim 1, characterized in that it forms a dispersion of PEBA dissolved in an oily phase dispersed in an aqueous phase in the presence of a surfactant.

10. The composition as claimed in claim 1, characterized in that it forms a dispersion of PEBA dissolved in an aqueous phase dispersed in an oily phase in the presence of a surfactant.

11. The composition as claimed in claim 1, said composition being a colored, non-colored and/or transparent product selected from the following products:
    makeup products for the face and the human body,
    care products for the face and the human body,
    hair products,
    perfumery products.

12. The composition as claimed in claim 11, that is foundation, tinted cream, loose or compact powder, eye shadow, mascara, eye liner, lipstick, nail varnish;
    cream, milk, lotion, mask, peeling product, cleansing and/or makeup removal products, deodorants, antiperspirants, shaving products, epilatories;
    shampoos, products for shaping the hair, styling products, anti-dandruff products, products against hair loss, products against dryness of the hair, hair dyes, bleaching products;
    perfume, milk, cream, or perfumed loose or pressed powder.

* * * * *